United States Patent [19]

Glassman

[11] 4,272,240

[45] Jun. 9, 1981

[54] ORTHODONTIC APPLIANCE FOR APPLYING A POWER FORCE TO A TOOTH

[76] Inventor: E. Glenn Glassman, 85 Paramus Rd., Paramus, N.J. 07652

[21] Appl. No.: 181,865

[22] Filed: Aug. 27, 1980

[51] Int. Cl.³ .............................................. A61C 7/00
[52] U.S. Cl. ...................................................... 433/18
[58] Field of Search ........................ 433/18, 24, 21, 17

[56] References Cited

U.S. PATENT DOCUMENTS

| 3,353,271 | 11/1967 | Blechman | 433/21 |
| 3,477,129 | 11/1969 | Rubin | 433/17 |

Primary Examiner—Robert Peshock
Attorney, Agent, or Firm—Ralph R. Roberts

[57] ABSTRACT

This invention pertains to an improved orthodontic appliance which includes a tubular member pivotally attached to a plate member. This plate member is attached to a band secured to a tooth of a patient. The tubular member is limited in its swing by detents provided on the plate. A power force, which may be a spring biased piston and wire shank or may be a headgear apparatus, is mounted in this pivoted tubular member. The biased piston module may be secured to a moulded retainer for removable use in the mouth of a patient. The pivoted tubular support enables easy removal of the power force for cleaning and adjustment. With a biased piston there is provided an adjustable stop so that a determined force may be applied during repositioning of a tooth.

11 Claims, 12 Drawing Figures

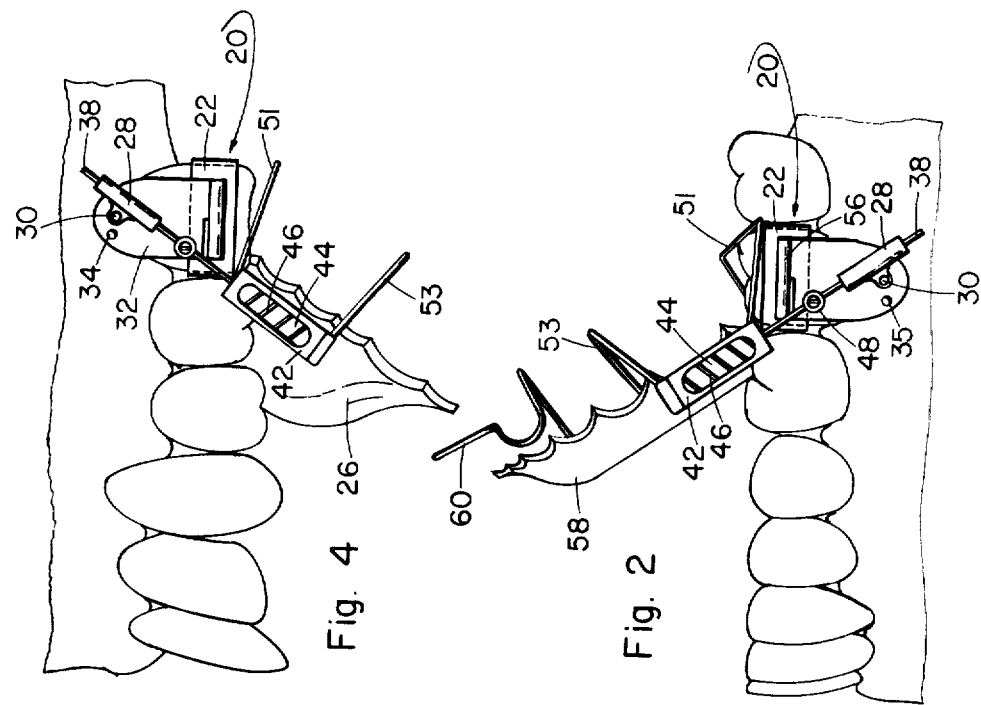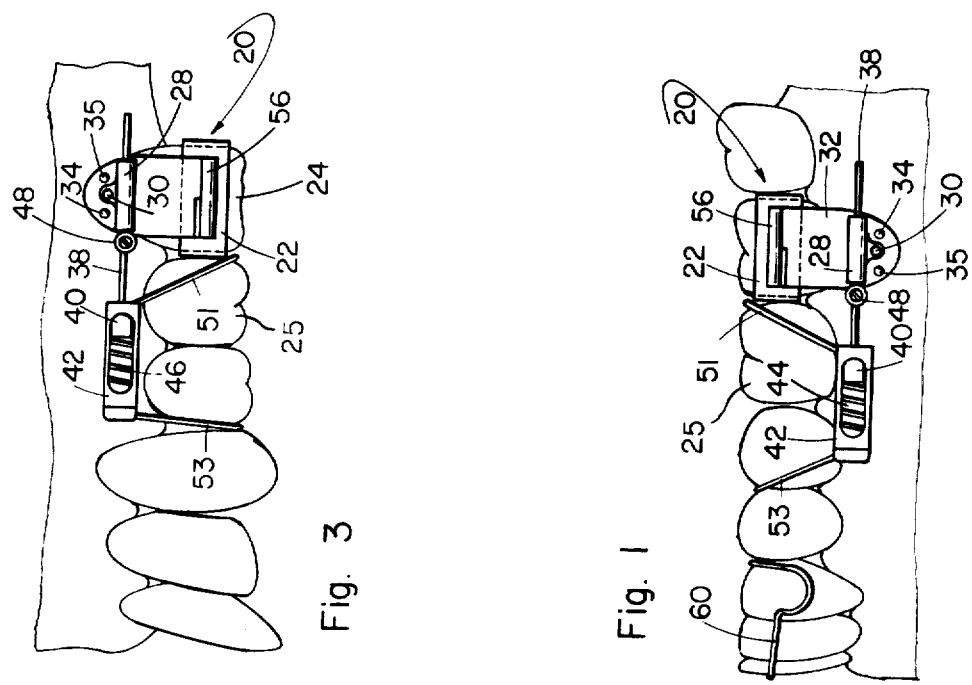

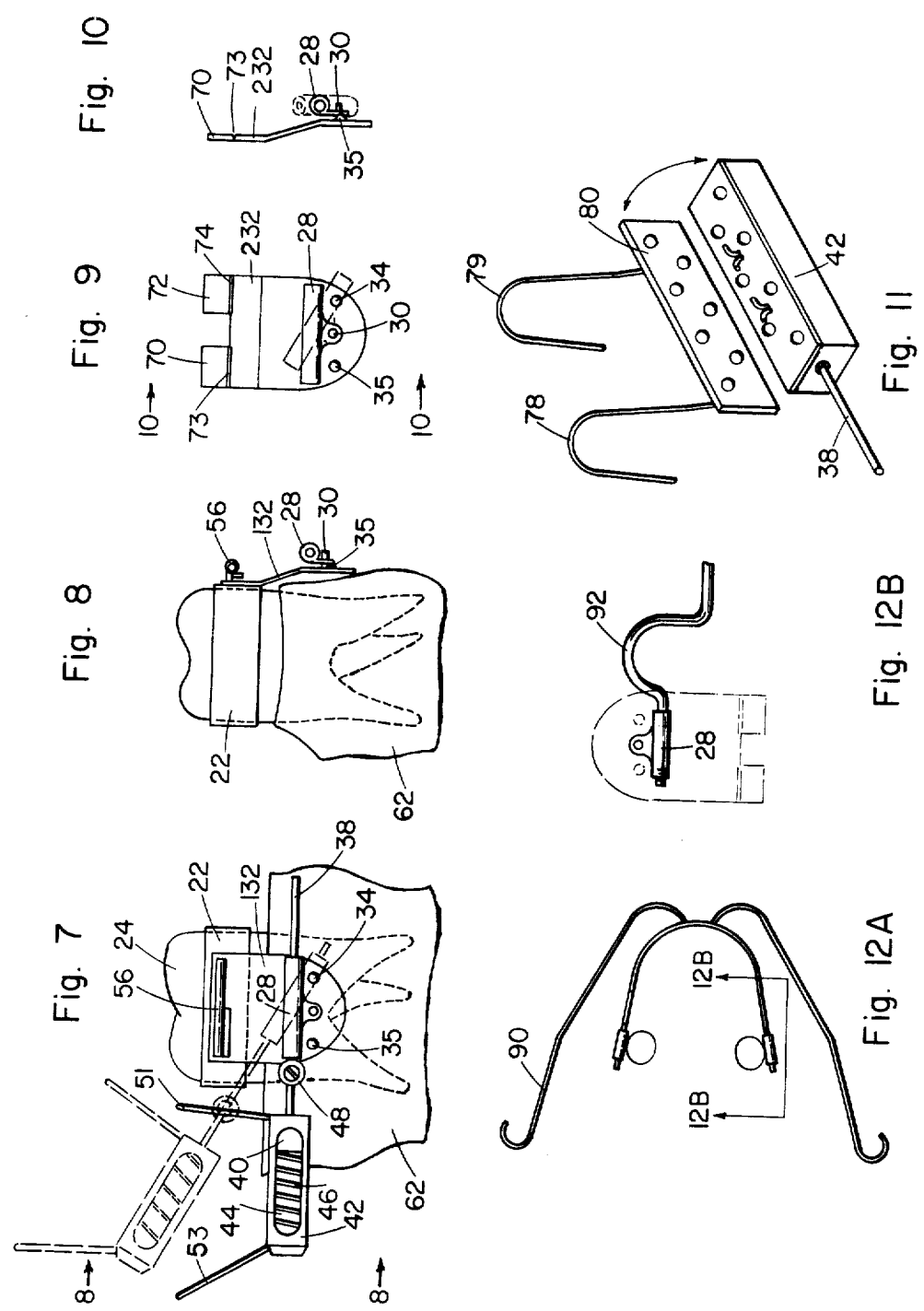

ORTHODONTIC APPLIANCE FOR APPLYING A POWER FORCE TO A TOOTH

BACKGROUND OF THE INVENTION

1. Field of the Invention

With reference to the classification of art as established in and by the United States Patent Office the present invention is in the General Class entitled, "Dentistry" (Class 433) and to the subclass entitled, "means to transmit or apply force to tooth"(subclass 18) and to the subclass entitled, "method of positioning or aligning teeth" (subclass 24).

2. Description of the Prior Art

The field of orthodontics is well known and the correcting of malocclusions, particular in juveniles, has been and is a problem requiring solution if the bite and appearance are to be corrected. Of course, orthodontics is not restricted to juveniles but is also known in adults although not as frequently. The moving of a molar or another tooth into a desired position has been and is a problem. In addition to wires and rubber bands the use of head gear is also well known. The moving of one or more teeth to a desired position is not a case of overnight application but requires a period of weeks or months of constant and direct pressure. Prior to this invention the moving of teeth has used wire braces and attachments.

In the present invention there is provided a bracket and band which has a swivel mounting. This band is attached to a tooth to be moved and is urged into its final position by means of a calibrated spring. The present invention proposes to provide an easy removal of the appliance and force with the pivoted retainer which is carried by a band on the tooth. Extraoral force is commonly used in class II malocclusions to correct a molar relationship to class I. This force depends upon the desired movement of the molars with high-pull, straight pull or cervical pull traction. Headgear anchorage is now used and is derived either from the occipital region of the skull or the cervical region of the neck. Straps are connected from these areas to a facebow which is connected to the maxillary molars and protrudes out of the side of the patients mouth.

Since patient cooperat5on and total appliance wear is a big factor in any orthodontic treatment, the more esthetic appliance of this invention is better tolerated by the patient and results in more efficious correction of the problem. In this regard a new intraoral force system utilizing palatal anchorage is provided to correct class II malocclusions.

Class II malocclusions comprise a large percentage of orthodontic deformities and the correction of this condition is of concern to all orthodontics. Correcting a class II malocclusion to a class I occlusion includes inhibiting forward maxillary growth, inhibiting forward movement of maxillary teeth, altering normal eruption of maxillary teeth, moving maxillary teeth posteriorly, stimulating horizontal and vertical growth of the mandible, altering eruption pattern of mandibular teeth, moving mandubular teeth forward on the skeletal base, repositioning the mandible forward and creating space to move teeth by selective extraction.

Attempts to influence the force in orthodontics include anchorage support and correction of dental relationships. Headgear is employed for extra-oral forces in order to obtain a more stable anchorage in the maxilla during the retraction of anterior teeth after the removal of first premolars in the treatment of the class II division I malocclusion.

SUMMARY OF THE INVENTION

This invention may be summarized, at least in part, with reference to its objects.

It is an object of this invention to provide, and it does provide, a band having a pivoted tubular receiver in which a wire form may be removably mounted for application of a directed force to a tooth.

It is a further object of this invention to provide, and it does provide, a pivoted retainer as attached to a band which is secured to a tooth, this pivoted retainer permitting removable application of force to the band holding the tooth.

In brief, this invention provides a pivoted retainer which includes a tubular passageway. This pivoted retainer is secured to a band fastened to a tooth which is to be moved or repositioned. This pivoted retainer provides a removable mounting of a force member within or without the mouth and application of said force to move the tooth to a desired position or condition. This pivoted retainer may be actuated by a spring which is carried by a removable plate. In use with the lower jaw there is provided a cutout to allow the tongue to function. In use with the upper jaw this retainer includes a removable arch member that utilizes suction to hold the spring actuated force members in place.

The pivoted retainer may be attached to a band as by welding or soldering. The spring force member may be attached as by epoxy cement. A headgear wire form carried on the outside of the head and having an inwardly directed wire protrusion end may engage the pivoted socket to move the tooth. It is also to be noted that this bracket may be provided with a stirrup or passageway in which a wire form is mounted for the moving of teeth as is often done in orthodontics.

In addition to the above summary the following disclosure is detailed to insure adequacy and aid in understanding of the invention. This disclosure, however, is not intended to cover each variation in form or addition of further improvements. For this reason there has been chosen a specific embodiment of a pivoted retainer as adopted for use with a force member and showing a preferred means for use in the mouth of a user. This specific embodiment has been chosen for the purposes of illustration and description as shown in the accompanying drawings wherein:

BRIEF DESCRIPTION OF THE DRAWINGS

FIG. 1 represents a side view, partly diagrammatic and showing retention apparatus for a lower jaw and a pivoted socket secured to a band;

FIG. 2 represents the orthodontic apparatus of FIG. 1 with the retainer swung into a pivoted condition for removal from the mouth of a patient, the removal permitting cleaning and adjustment;

FIG. 3 represents a side view of a pivoted retainer affixed to a band and shown on an upper tooth, this pivoted bracket moved by a spring carried by wires which may be embedded in a molded retainer;

FIG. 4 represents a side view of the appliance of FIG. 3 with the retainer swung into a pivoted condition for removal from the mouth of a patient, the removal permitting cleaning and adjustment;

FIG. 7 represents a pivoted bracket secured to the band of the tooth and showing a spring loaded appliance adapted for mounting to two or more teeth of a user;

FIG. 8 represents a diagrammatic, partial end view of FIG. 7 taken on the line 8—8 of FIG. 7 and looking in the direction of the arrows;

FIG. 9 represents a side view of a pivoted bracket which is attachable to the band as by means of spot welding and providing easy means for removal by the orthodontist after the desired period of use;

FIG. 10 represents a side view of the bracket of FIG. 9, this view taken on the line 10—10 of FIG. 9 and looking in the direction of the arrows;

FIG. 11 represents an exploded isometric view, partly diagrammatic and showing a means for attaching a spring module to support means by epoxy cement, and FIGS. 12 A and 12 B represent the use of the pivoted bracket affixed on bands with a headgear wire form used as a force means.

In the following description and in the claims various details are identified by specific names for convenience. These names are intended to be generic in their application. Corresponding characters refer to like members throughout the several figures of the drawings.

DESCRIPTION OF THE EMBODIMENT OF FIGS. 1 THROUGH 6

Figure 5:
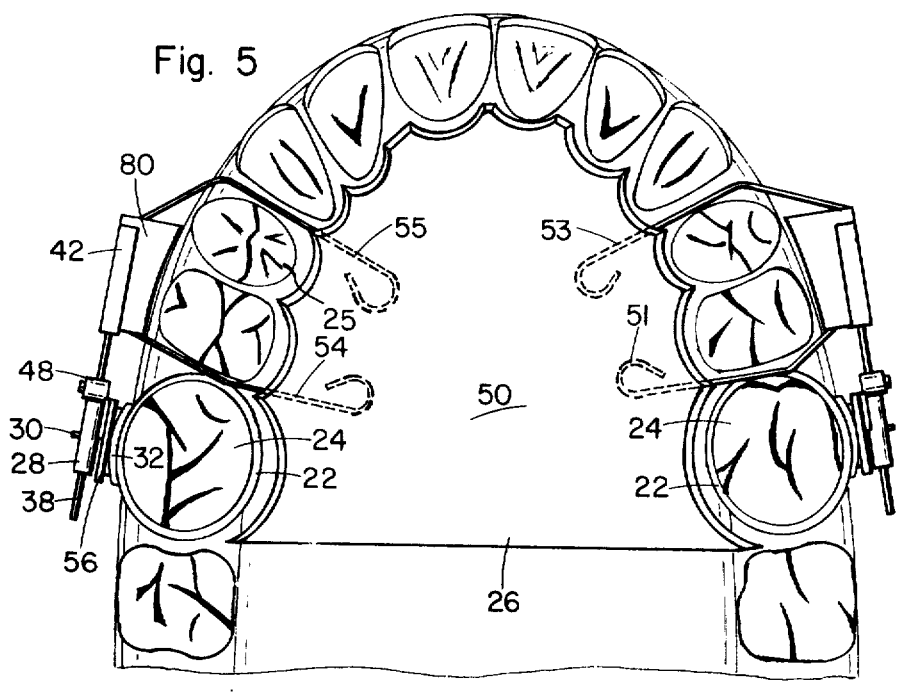
FIG. 5 represents a plan view in an enlarged scale of the applicance of FIG. 3 as mounted in the roof of the mouth of the user and showing in particular the relationship of the spring actuated force and the pivoted socket.

Referring next to the drawings and in particular to FIGS. 1 through 6, there is shown a force means for moving one or more teeth to reposition the teeth and provide the desired bite. A pivoted retainer, generally identified as 20, is attached to a band 22 that is secured to a tooth 24. This tooth is repositioned to mate with a tooth in the opposite jaw. Adjacent teeth 25 may be utilized or a molded and fitted retainer 26 may be used in this movement of a tooth 24.

A tubular member 28 provides a passageway therethrough and as a member is pivotally retained by a pin 30 on a formed plate member 32. Dimples 34 and 35 protrude from the surface of said member and provide stops that limit the turning of the tubular member 28. The size and position of these dimples 34 and 35 are merely a matter of selection. Dimples need not be formed since other outwardly extending means such as beads or tabs may also be provided. This member 28 is secured to a band 22 at its upper edge.

Carried in and by the tubular member 28 is a wire shank 38 of a piston or slidable member 40 carried in a hollow support 42. For adjustment and cleaning a window slot 44 is provided in support 42. A compression spring 46 is provided in this support and urges the piston 40 toward the right end as in FIG. 1. On the extending wire shank 38 is a screw stop 48. This stop may employ either a slotted screw or socket headed screw but whichever screw is used this stop is tightened to secure the stop in the wire shank 38 at a selected position as to be described hereinafter.

In FIGS. 3, 4 and 5 the fitted retainer 26 is shown. This retainer is usually of plastic and is molded to fit tightly in the mouth of the user. In these FIGS. the invention is directed toward use in the upper mouth of the user. The central portion 50 is molded to utilize the suction provided with the pallet of the user. Wires 51, 53, 54 and 55 (FIG. 5) are shown as embedded in this formed retainer. The forward portion of said molding is contoured and/or trimmed to avoid the teeth of the user.

Figure 6:
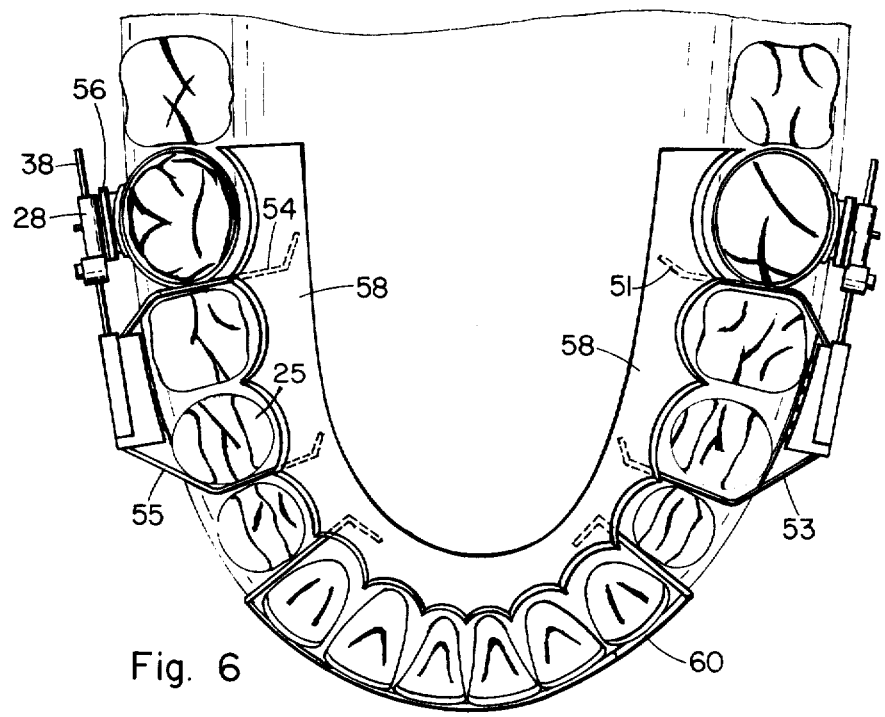
FIG. 6 represents a plan view in the scale of FIG. 5 and depicting an appliance as carried by a molded retainer shaped and adapted for a lower jaw.

In FIGS. 5 and 6 the showing includes each plate member to also carry a wire form attachment 56 for the use of additional wires as conventionally provided by an orthodontist.

EMBODIMENT OF FIGS. 1, 2 AND 6

Referring next to FIGS. 1, 2 and 6, there is depicted the tubular member 28 and pin 30 on the formed plate member 32. Wires 51 and 53 may be employed for retaining by adjacent teeth 25. Shown in this view is the attachment 56 by which an additional and conventional wire form may be provided and used.

Referring next to FIG. 6, it is to be noted that the arrangement of FIG. 5 may also be used in the lower jaw of the user. As shown, the formed retainer 26 has a removed central portion which accommodates the tongue. This retainer 58 may and preferably does include a retaining wire 60 that engages the forward and outside of the teeth in the front of the jaw of the user. A lower retainer 126 has no suction as is provided by a pallet so the wire 60 is often required and desired.

EMBODIMENT OF FIGS. 7 AND 8

Referring next to the embodiment of FIGS. 7 and 8, it is to be noted that the plate member is bent so that it lies adjacent an outside gum 62 of the patient. This bent plate member is identified as 132 and the contour is adjusted by the orthodontist. Band 22 is secured to a tooth 25 and depicted is the wire attachment and retainer that may also be utilized by the orthodontist. The pivoted tubular member 28 is shown as receiving and retaining the wire shank 38 in support 42. The piston 40 and spring 46 are also shown.

EMBODIMENT OF FIGS. 9 AND 10

Referring next to FIGS. 9 and 10, it is to be noted that the plate member, now identified as 232, may be made with tab portions 70 and 72 which are spot welded to the band 22, or if desired, attached by means such as soldering or epoxy cement. After the desired period of use the orthodontist can and may remove the tubular pivoted member 28 by bending at the score lines 73 and 74 to cause the plate member to break off. This tubular member 28 and plate member 232 are now discarded without disturbing the band 22.

EMBODIMENT OF FIG. 11

Referring next to FIG. 11, it is to be noted that the attaching or mounting of a spring force as by epoxy cement anticipates that wires 78 and 79 are carried on pad member 80. This pad has a face especially adapted for attachment by spring housing 142. This spring housing is glued in place after the molded and fitted retainer 26 is in place. The attaching, as by epoxy cement, enables a desired placement and/or angle to be provided to apply a determined force on the tooth to be moved or repositioned.

EMBODIMENT OF FIGS. 12 A AND 12 B

Referring next and finally to FIGS. 12 A and 12 B, it is to be noted that a headgear wire form 90 may be used instead of the spring actuated power force. With a headgear wire form 90 the pivoted tubular member 28 is secured to a band 22 in the manner above described. Rather than the spring force in support 42 the force is applied through the wire form 90. Conventionally, headgear applications include straps, elasticized and with resilient means. The headgear wire form is contemplated to be used only when upper teeth are to be moved. For this purpose there is provided a bend 92 in the wire form. The cervical traction headgear is the most popular form of extra-oral appliance in orthodontics today. Unfortunately in some patients this appliance is found to have undesirable side effects. These include upper molar extrusion, exacerbating an open bite and causing the mandible to rotate in a clockwise direction thereby increasing lower facial height and worsening a class II profile. Distal tipping of upper first molars with cervical therapy is also present. The straight pull headgear provides forces that are actually five to ten degrees above the occlusal plane. With this force there is an inherent tipping and intrusive vector. For these reasons the use of headgear in the present invention is used with caution.

USE AND OPERATION

The above embodiments anticipate the use of stainless steel in the hollow support 42. This support is mounted in the acrylic moulding which holds the retentive wire portions. The moulding or mouldings are adjusted so as to rest anterior to the first molars. These wires are contemplated to fall occlusally and interproximally between the cuspid and first bicuspid and the second bicuspid and molar. The tubular member 28 allows the appliance to be removable while the spring module is calibrated to deliver sixteen ounces of force. Molar bands 22 with spot welded tubular members are cemented to first molars. Maxillary casts, a layer of acrylic 1-2 millimeters thick, are placed over the palate and extend to the cervical regions.

Once the acrylic portion of the appliance have been smoothed and polished it is inserted into the mouth and the spring module is then adjusted. The shank wire 38 of the unactivated spring is placed through the tubular member so that it extends at least three millimeters from the distal end of the tubular member. The spring and shank wire is aligned parallel to the occlusal plane. Either acrylic or banding material secures the support 42 in place and is fastened in this position. Once setting had occurred the shank wire would be cut so that not more than three millimeters extends distal to the tubular member. The appliance is removed from the mouth and the moulded anchor plate of plastic is trimmed and smoothed. The patient is then instructed in placement and use of the appliance.

Activation of the force is achieved intraorally by pushing the end of the power arm into the distal end of the tubular member. An indicator on the power arm on the end of the piston module window is aligned with a corresponding indicator on the outside of the window. The screw lock is moved along the power arm and tightened against the mesial portion of the tubular member. The force module is now in application.

Terms such as "left", "right", "up", "down", "bottom", "top", "front", "back", "in", "out", "clockwise", "counterclockwise" and the like are applicable to the embodiments shown and described in conjunction with the drawings. These terms are merely for the purposes of description and do not necessarily apply to the position in which the orthodontic appliance may be constructed or used.

While particular embodiments of the power force and pivoted tubular member have been shown and described it is to be understood the invention is not limited thereto since modifications may be made within the scope of the accompanying claims and protection is ought to the broadest extent the prior art allows.

What is claimed is:

1. An orthodontic appliance for applying a power force to a tooth and including:
    (a) a band secured to a tooth which is to be moved and/or repositioned by the application of a power force to said tooth;
    (b) a plate member secured to this band and adapted to lay alongside the outside of said tooth and below said band;
    (c) a tubular member providing a passageway therethrough of a selected size, said tubular member pivotally secured to the extending portion of said plate member;
    (d) means for limiting the pivotal movement of said tubular member, said limiting means providing means for tilting the tubular member to a selected limit;
    (e) a power force removably carried in or on the head of the user, this power force including a wire member slidable in the through passageway, and
    (f) means for limiting the travel of the power force wire in said tubular member so that a directed and desired movement of the tooth is made when the power force is positioned within this pivoted tubular member, the removal of said power force easily achieved when the power force is tilted for removal from the mouth.

2. An orthodontic appliance as in claim 1 in which the power force includes a piston slidable in a hollow support, this piston having a wire shank portion extending from one end of the hollow support and with the piston biased toward the end from which the wire shank extends.

3. An orthodontic appliance as in claim 2 in which the bias is a compression spring.

4. An orthodontic appliance as in claim 3 in which the hollow support has a viewing window formed in its side extent.

5. An orthodontic appliance as in claim 3 in which the means for limiting the pivotal movement of the tubular member are protrusions carried by the plate member, said protrusions adapted to engage the tubular member at said limits of movement.

6. An orthodontic appliance as in claim 3 in which the power force and the hollow support are carried by wires embedded in a moulded retainer that is removably mounted interior of the teeth of the user.

7. An orthodontic appliance as in claim 3 in which the hollow support is attached to the moulded retainer as by epoxy cement.

8. An orthodontic appliance as in claim 1 in which the plate member is attached to the band by welding, soldering, cement and the like, the attaching portion being tab portions weakened or scored for easy separation from the band absent removal of the band from the tooth.

9. An orthodontic appliance as in claim 1 in which the plate member is also provided with additional attaching and supporting means for other wire forms that are substantially secured for long durations in the mouth of the user.

10. An orthodontic appliance as in claim 1 in which the plate member is bent so that in a mounted condition the plate lies adjacent the tooth and gum of the user.

11. An orthodontic appliance as in claim 1 in which the passageway through the pivoted tubular member is adapted to receive and retain the wire form ends of a headgear whose inwardly extending ends are bent to provide a stop and direction of applied force.

* * * * *